(12) United States Patent
Kondou

(10) Patent No.: US 10,912,905 B2
(45) Date of Patent: Feb. 9, 2021

(54) OXYGEN CONCENTRATING APPARATUS

(71) Applicant: DAIKIN INDUSTRIES, LTD., Osaka (JP)

(72) Inventor: Keita Kondou, Osaka (JP)

(73) Assignee: Daikin Industries, Ltd., Osaka (JP)

(*) Notice: Subject to any disclaimer, the term of this patent is extended or adjusted under 35 U.S.C. 154(b) by 372 days.

(21) Appl. No.: 15/776,358

(22) PCT Filed: Oct. 18, 2016

(86) PCT No.: PCT/JP2016/080834
§ 371 (c)(1),
(2) Date: May 15, 2018

(87) PCT Pub. No.: WO2017/086075
PCT Pub. Date: May 26, 2017

(65) Prior Publication Data
US 2020/0254200 A1      Aug. 13, 2020

(30) Foreign Application Priority Data
Nov. 16, 2015   (JP) .................. 2015-223699

(51) Int. Cl.
| | |
|---|---|
| *A61M 16/00* | (2006.01) |
| *A61M 16/06* | (2006.01) |
| *A61M 16/10* | (2006.01) |
| *A61M 16/08* | (2006.01) |
| *G08B 17/12* | (2006.01) |

(52) U.S. Cl.
CPC .... *A61M 16/0087* (2013.01); *A61M 16/0003* (2014.02); *A61M 16/022* (2017.08);
(Continued)

(58) Field of Classification Search
CPC .............. A61M 16/10; A61M 16/1005; A61M 16/101; A61M 16/0087; A61M 16/0003;
(Continued)

(56) References Cited

U.S. PATENT DOCUMENTS 5,282,464 A * 2/1994 Brain ................ A61B 5/14552
                                                        128/207.15
5,911,219 A * 6/1999 Aylsworth ............ A61M 16/20
                                                        128/205.23
(Continued)

FOREIGN PATENT DOCUMENTS

DE   202012009706 U1 * 6/2013 .......... A61M 16/202
JP   2001-314507 A    11/2001
(Continued)

OTHER PUBLICATIONS

International Preliminary Report of corresponding PCT Application No. PCT/JP2015/080834 dated May 22, 2018.
(Continued)

*Primary Examiner* — David Colon-Morales
(74) *Attorney, Agent, or Firm* — Global IP Counselors, LLP

(57) ABSTRACT

An oxygen concentrating apparatus includes an oxygen supply source, an attaching member, and a photodetector. An oxygen discharger is attached to the attaching member while oxygen from the oxygen supply source is supplied to the oxygen discharger. The photodetector is disposed in the oxygen concentrating apparatus and on an extension of an oxygen supply passage of the attaching member.

12 Claims, 7 Drawing Sheets

(52) U.S. Cl.
CPC .... *A61M 16/0672* (2014.02); *A61M 16/0875* (2013.01); *A61M 16/101* (2014.02); *G08B 17/12* (2013.01); *A61M 2205/3306* (2013.01); *A61M 2205/3334* (2013.01); *A61M 2205/3368* (2013.01)

(58) Field of Classification Search
CPC ............ A61M 16/022; A61M 16/0875; A61M 2205/3306; A61M 2205/3368; A61M 2202/0208; Y10T 137/1842; Y10T 137/1939; Y10T 137/1963; Y10T 137/1987
See application file for complete search history.

(56) References Cited

U.S. PATENT DOCUMENTS

| | | | | |
|---|---|---|---|---|
| 8,393,323 | B2* | 3/2013 | Andrieux | A61M 16/12 128/204.21 |
| 2013/0008438 | A1* | 1/2013 | Sugawara | A61M 16/0672 128/202.24 |
| 2013/0299005 | A1 | 11/2013 | Enomoto et al. | |
| 2016/0029973 | A1* | 2/2016 | Kahlman | A61B 5/015 600/301 |
| 2017/0319802 | A1* | 11/2017 | Holder | A61M 16/0666 |
| 2018/0085544 | A1* | 3/2018 | Holyoake | A61M 16/01 |

FOREIGN PATENT DOCUMENTS

| | | |
|---|---|---|
| JP | 2008-136663 A | 6/2006 |
| JP | 3145485 U | 9/2008 |
| JP | 2010-178939 A | 8/2010 |
| WO | 2010/013402 A1 | 2/2010 |
| WO | 2012/066784 A1 | 5/2012 |

OTHER PUBLICATIONS

International Search Report of corresponding PCT Application No. PCT/JP2016/080834 dated Dec. 27, 2016.

* cited by examiner

REARWARD ⟷ FORWARD

REARWARD  FORWARD

OXYGEN CONCENTRATING APPARATUS

CROSS-REFERENCE TO RELATED APPLICATIONS

This U.S. National stage application claims priority under 35 U.S.C. § 119(a) to Japanese Patent Application No. 2015-223699, filed in Japan on Nov. 16, 2015, the entire contents of which are hereby incorporated herein by reference.

BACKGROUND

Field of the Invention

The present invention relates to an oxygen concentrating apparatus configured to supply oxygen from an apparatus main body to an oxygen discharger.

Background Information

To perform oxygen inhalation therapy for a patient with a chronic respiratory disease, an instrument termed cannula is used for inhaling, through the nose, oxygen supplied from an oxygen concentrating apparatus. An example of the oxygen concentrating apparatus configured to supply oxygen to the cannula is an adsorption-type oxygen concentrating apparatus recited in Japanese Unexamined Patent Publication No. 2008-136663, which is configured to generate concentrated oxygen gas by adsorbing nitrogen in the air.

When, for example, the ambient temperature of the cannula becomes significantly high on account of fire or the like and the discharge of oxygen from an outlet of a cannula attaching portion is stopped, the oxygen concentrating apparatus may be powered off by operating a power switch.

SUMMARY

The oxygen concentrating apparatus of Japanese Unexamined Patent Publication No. 2008-136663 is disadvantageous in that oxygen discharge cannot be properly stopped when the fire is unnoticed.

The present invention has been done to solve this problem, and an object of the present invention is to provide an oxygen concentrating apparatus which is able to reliably detect fire on a cannula.

According to a first aspect of the invention, an oxygen concentrating apparatus includes:
an oxygen supply source;
an attaching member to which an oxygen discharger is attached at a time of supplying oxygen from the oxygen supply source to the oxygen discharger; and
a photodetector which is provided in the oxygen concentrating apparatus and on an extension of an oxygen supply passage of the attaching member.

In this oxygen concentrating apparatus, the photodetector is provided in the oxygen concentrating apparatus and on an extension of the oxygen supply passage of the attaching member. In other words, the photodetector is upstream of the attaching member in the flow direction of the oxygen. Because smoke generated by fire on the oxygen discharger flows downstream in the flow direction of the oxygen, light is detectable, without being blocked by the smoke, by the photodetector which is provided upstream in the flow direction of the oxygen, with the result that the detection of the fire is ensured. The supply of the oxygen is therefore properly stopped. Furthermore, because the photodetector is provided on the extension of the oxygen supply passage and hence light generated by fire is not blocked by the oxygen supply passage, the photodetector is able to reliably detect the fire.

According to a second aspect of the invention, the oxygen concentrating apparatus is arranged such that, when the photodetector detects fire on the oxygen discharger, supply of the oxygen is stopped.

In this oxygen concentrating apparatus, when the photodetector detects fire on the oxygen discharger, the supply of the oxygen is properly stopped.

According to a third aspect of the invention, the oxygen concentrating apparatus is arranged such that an opaque transmission window which allows light to pass is provided between the oxygen supply passage and the photodetector, and
the photodetector detecting light through the transmission window is an optical sensor capable of detecting an infrared region.

In this oxygen concentrating apparatus, the transmission window which is opaque and blocks visible light is provided, and an optical sensor which is a photo diode or the like capable of detecting an infrared region is used as the photodetector. For this reason, influences of ambient light such as sunlight and illumination light are restrained and erroneous detection is prevented as compared to cases where a visible light sensor configured to receive only visible light is employed. Furthermore, because the transmission window is provided between the oxygen supply passage and the photodetector, adhesion of impurities such as dust to the photodetector is prevented.

According to a fourth aspect of the invention, the oxygen concentrating apparatus is arranged such that the attaching member is made of metal and includes a temperature sensor.

In this oxygen concentrating apparatus, the attaching member is made of metal with a high thermal conductivity, and the temperature sensor is provided. It is therefore possible to detect fire by heat, in addition to the photodetector.

According to a fifth aspect of the invention, the oxygen concentrating apparatus is arranged such that the oxygen supply passage includes a bent portion which is bent at right angle, and
an opaque transmission window which allows light to pass and is provided between the oxygen supply passage and the photodetector is provided at the bent portion.

In this oxygen concentrating apparatus, the oxygen supply passage is bent at right angle and is therefore compactly disposed.

According to a sixth aspect of the invention, the oxygen concentrating apparatus is arranged such that the oxygen supply passage includes at least a first passage formed in the attaching member, and
the photodetector is provided upstream in a flow direction of the oxygen flowing in the first passage.

In this oxygen concentrating apparatus, the photodetector is provided upstream in the flow direction of the oxygen flowing in the first passage. Because smoke generated by fire on the oxygen discharger flows downstream in the flow direction of the oxygen, light is detectable, without being blocked by the smoke, by the photodetector which is provided upstream in the flow direction of the oxygen, with the result that the detection of the fire is ensured.

According to a seventh aspect of the invention, the oxygen concentrating apparatus further includes
a connecting member connected to the attaching member, the oxygen supply passage including at least the first passage and a second passage which linearly communicates with the first passage and is formed in the connecting member, and the photodetector being provided upstream in the flow direction of the oxygen flowing in the second passage and the first passage in order.

In this oxygen concentrating apparatus, the photodetector is provided upstream in the flow direction of the oxygen flowing in the second passage and the first passage in order. Because smoke generated by fire on the oxygen discharger flows downstream in the flow direction of the oxygen, light is detectable, without being blocked by the smoke, by the photodetector which is provided upstream in the flow direction of the oxygen, with the result that the detection of the fire is ensured.

According to the first aspect of the invention, the photodetector is provided in the oxygen concentrating apparatus and on an extension of the oxygen supply passage of the attaching member. In other words, the photodetector is upstream of the attaching member in the flow direction of the oxygen. Because smoke generated by fire on the oxygen discharger flows downstream in the flow direction of the oxygen, light is detectable, without being blocked by the smoke, by the photodetector which is provided upstream in the flow direction of the oxygen, with the result that the detection of the fire is ensured. Furthermore, because the photodetector is provided on the extension of the oxygen supply passage and hence light generated by fire is not blocked by the oxygen supply passage, the photodetector is able to reliably detect the fire.

According to the second aspect of the invention, when the photodetector detects fire on the oxygen discharger, the supply of the oxygen is properly stopped.

According to the third aspect of the invention, the transmission window which is opaque and blocks visible light is provided, and an optical sensor which is a photo diode or the like capable of detecting an infrared region is used as a photodetector. For this reason, influences of ambient light such as sunlight and illumination light are restrained and erroneous detection is prevented as compared to cases where a visible light sensor configured to receive only visible light is employed. Furthermore, because the transmission window is provided between the oxygen supply passage and the photodetector, adhesion of impurities such as dust to the photodetector is prevented.

According to the fourth aspect of the invention, the attaching member is made of metal with a high thermal conductivity, and the temperature sensor is provided. It is therefore possible to detect fire by heat, in addition to the photodetector.

According to the fifth aspect of the invention, the oxygen supply passage is bent at right angle and is therefore compactly disposed.

According to the sixth aspect of the invention, the photodetector is provided upstream in the flow direction of the oxygen flowing in the first passage. Because smoke generated by fire on the oxygen discharger flows downstream in the flow direction of the oxygen, light is detectable, without being blocked by the smoke, by the photodetector which is provided upstream in the flow direction of the oxygen, with the result that the detection of the fire is ensured.

According to the seventh aspect of the invention, the photodetector is provided upstream in the flow direction of the oxygen flowing in the second passage and the first passage in order. Because smoke generated by fire on the oxygen discharger flows downstream in the flow direction of the oxygen, light is detectable, without being blocked by the smoke, by the photodetector which is provided upstream in the flow direction of the oxygen, with the result that the detection of the fire is ensured.

DETAILED DESCRIPTION OF EMBODIMENT(S)

The following will describe an embodiment of the present invention with reference to attached drawings.

Figure 1:
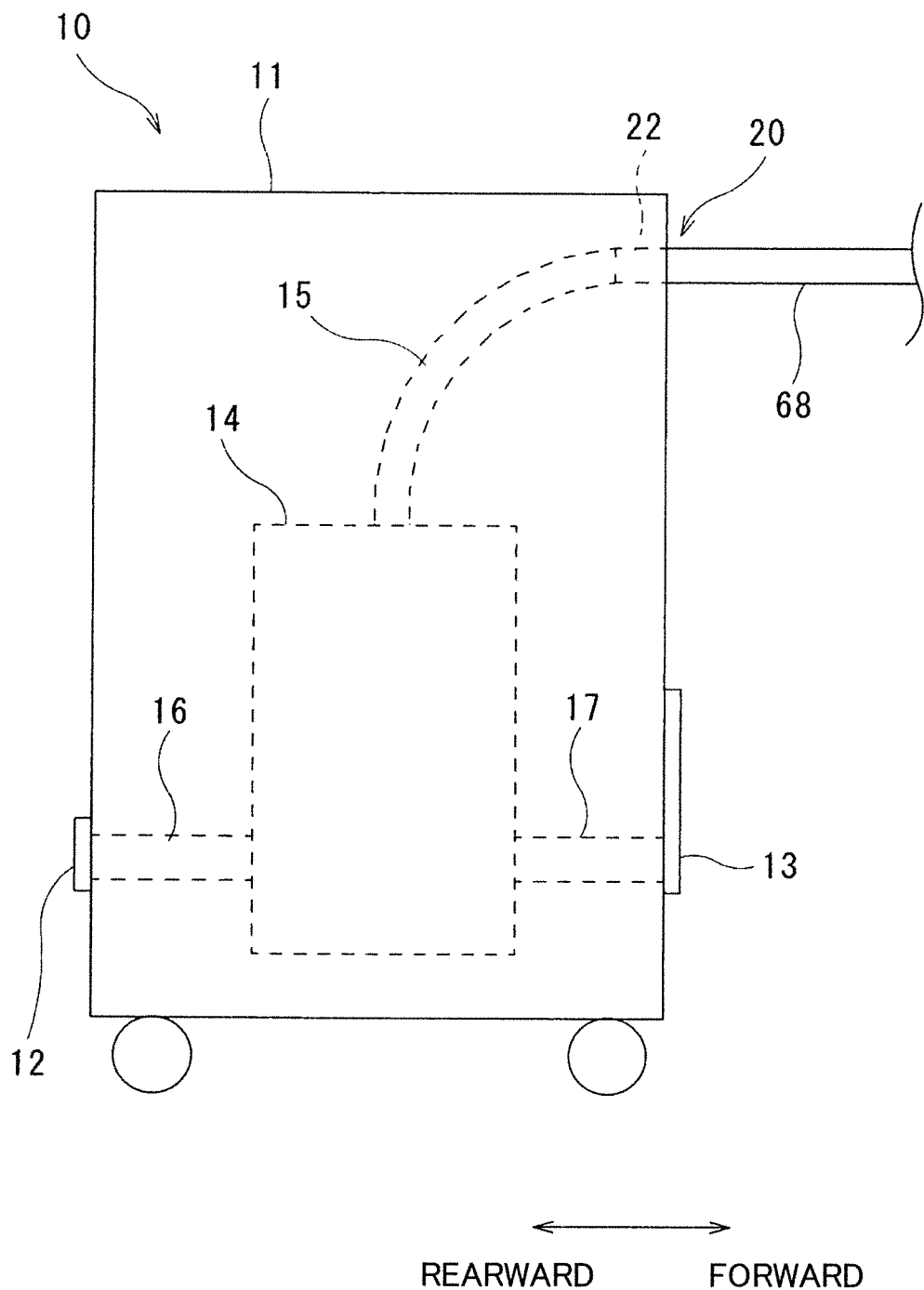
FIG. 1 is a schematic view of an oxygen concentrating apparatus of an embodiment of the present invention.

As shown in FIG. 1, an oxygen concentrating apparatus 10 of the present embodiment is connected to a cannula (oxygen discharger) 68 which is used for allowing a patient receiving oxygen inhalation therapy to inhale oxygen through the nose, and the oxygen concentrating apparatus 10 supplies oxygen to the cannula 68. The oxygen concentrating apparatus 10 may be connected to an instrument for discharging oxygen, which is not a cannula.

The oxygen concentrating apparatus 10 includes an apparatus main body 11 and an oxygen supplier 20 provided for the apparatus main body 11. In the apparatus main body 11, an air inlet port 13 and an exhaust port 12 are formed. The apparatus main body 11 further includes an oxygen generator (oxygen supply source) 14 configured to generate concentrated oxygen gas and an intermediate passage 15 connecting the oxygen generator 14 to the oxygen supplier 20.

The oxygen generator 14 of the present embodiment is configured to generate concentrated oxygen gas by means of an adsorbent such as zeolite, which adsorbs nitrogen under a high pressure and desorbs the adsorbed nitrogen under a low pressure. In other words, the oxygen generator is configured to generate concentrated oxygen gas by compressing air taken in from the outside through the air inlet port 13 and an air sucking passage 17, and adsorbing nitrogen in the compressed air. The nitrogen desorbed from the adsorbent under a low pressure is exhausted to the outside thorough an exhaust passage 16 and the exhaust port 12. Meanwhile, the concentrated oxygen gas generated by the oxygen generator 14 is discharged from the oxygen supplier through an intermediate passage 15. In FIG. 1, the direction toward the air inlet port 13 from the exhaust port 12 via the oxygen generator 14 is forward, and the opposite direction is rearward.

Figure 2:
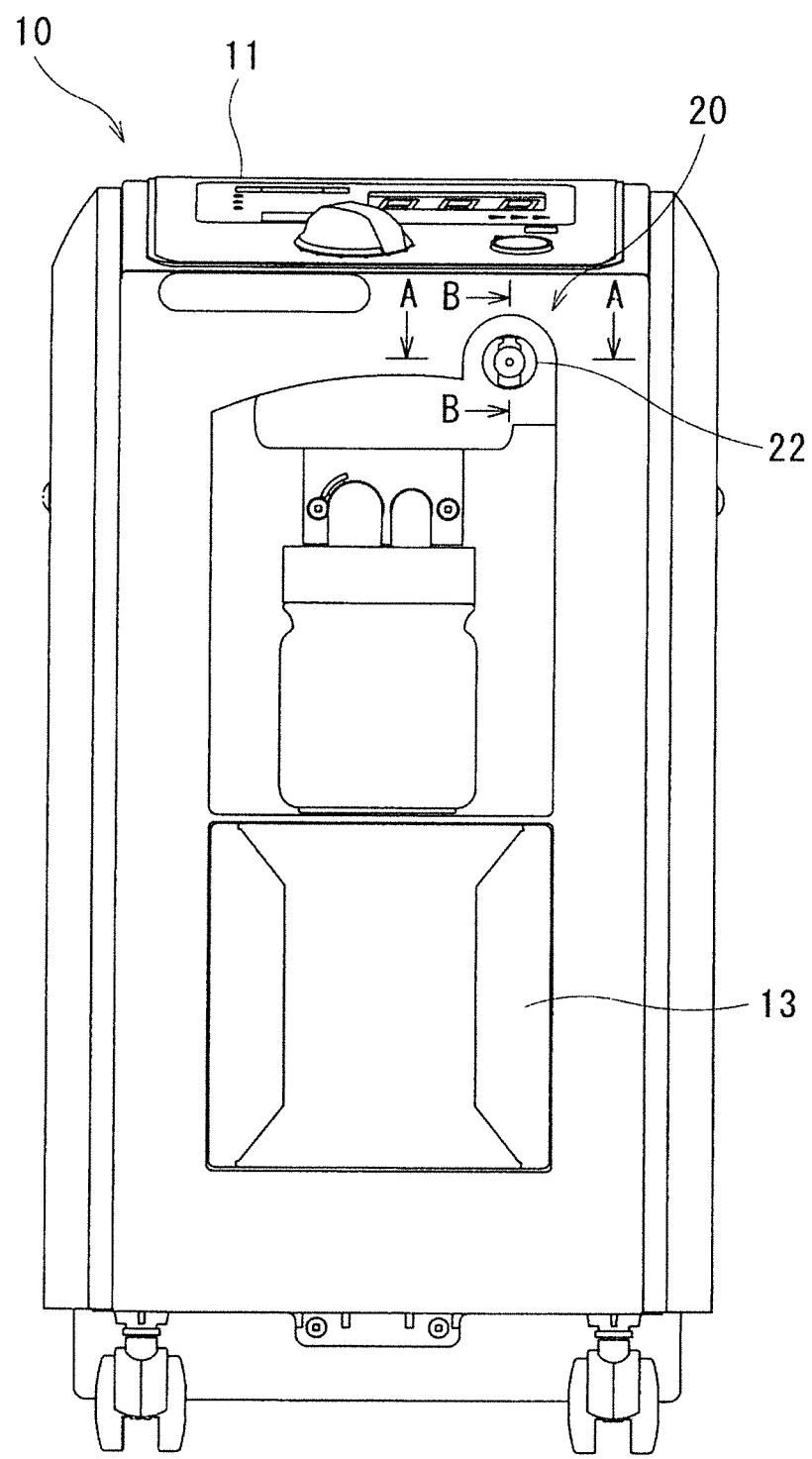
FIG. 2 is a front view of the oxygen concentrating apparatus shown in FIG. 1.

As shown in FIG. 2, the oxygen supplier 20 is provided at an upper part of the front surface of the apparatus main body 11. As shown in FIG. 3 to FIG. 6B, the oxygen supplier 20 includes an attaching member 22, a connecting member 30, an optical sensor 61 which is a photodetector capable of detecting an infrared region, and a fixed plate 60.

Figure 3:
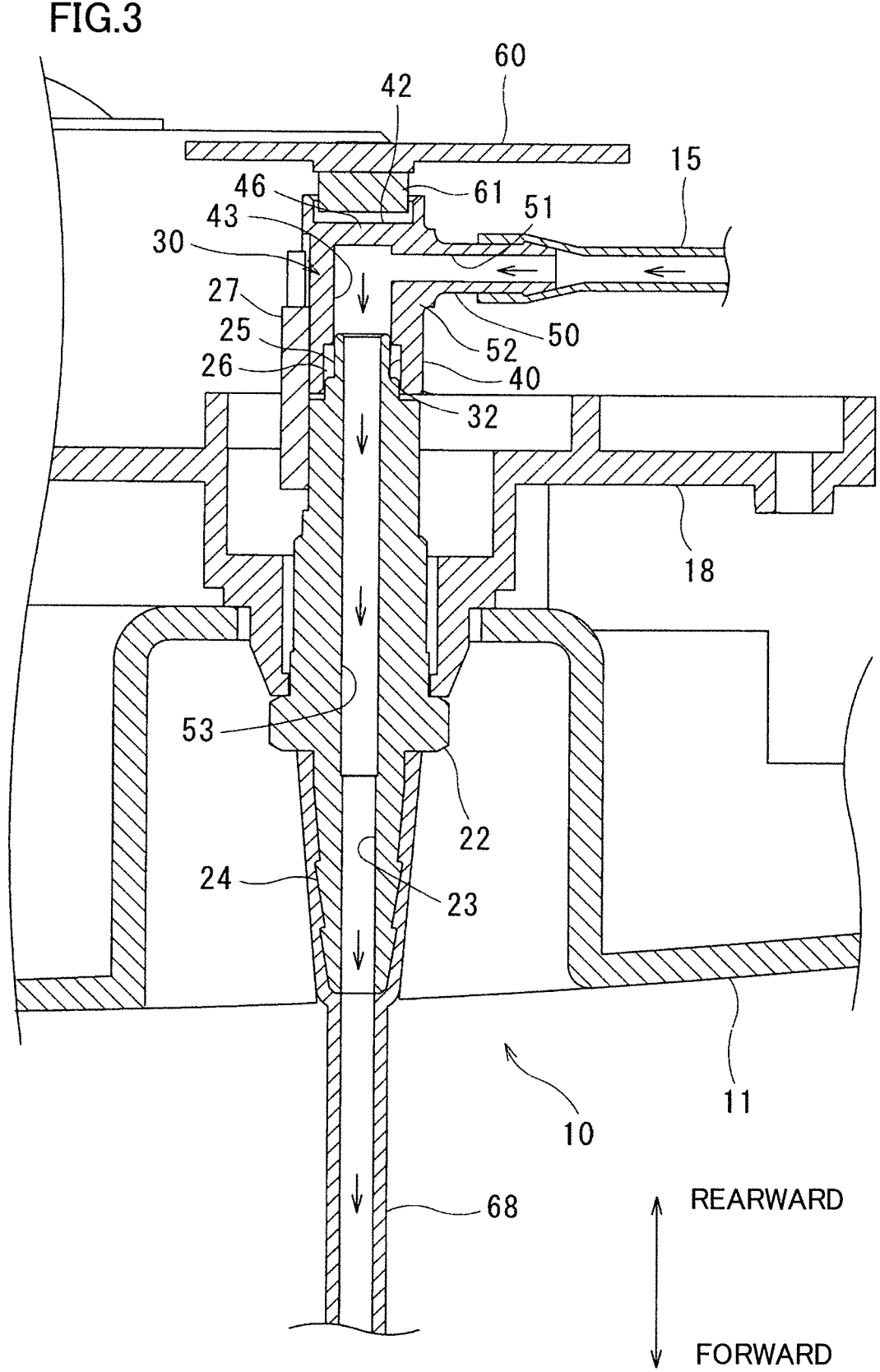
FIG. 3 is a cross section taken along a line A-A in FIG. 2.
Figure 4A:
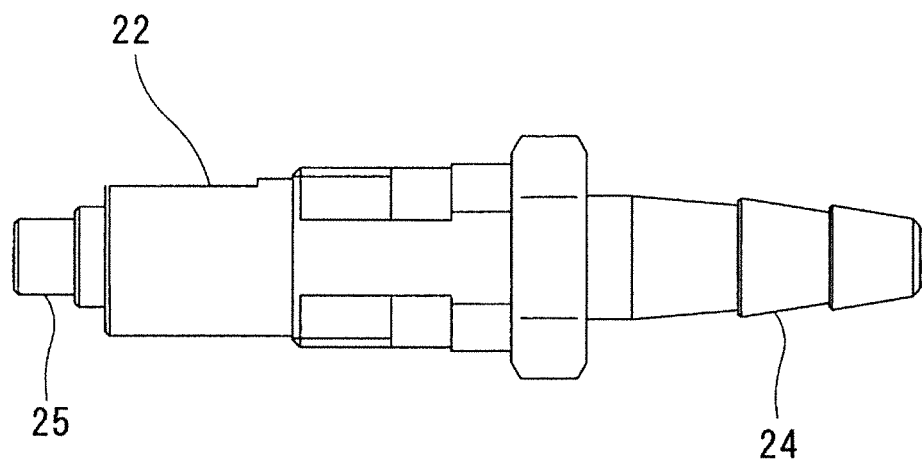
FIG. 4A is a side view of an attaching member.
Figure 4B:
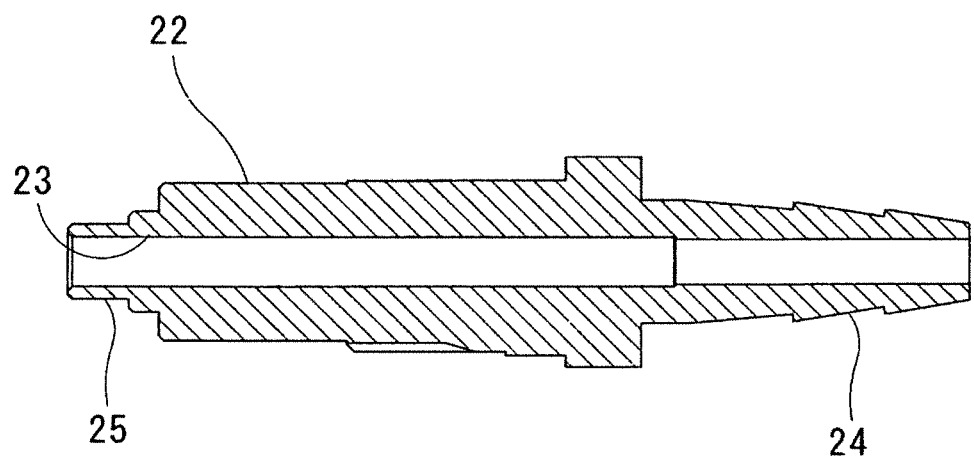
FIG. 4B is a cross section of FIG. 4A.

As shown in FIG. 4A and FIG. 4B, the attaching member 22 is a cylindrical nozzle extending in the axial direction. In this attaching member 22, a first passage 23 constituting a part of a later-described oxygen supply passage 53 is formed. The attaching member 22 is made of metal with a high thermal conductivity, and is attached to the apparatus main body 11 to be horizontal. When the attaching member 22 is attached to the apparatus main body 11 as shown in FIG. 3, the attaching member 22 is supported by an exterior cover 18 which covers internal components. The cannula 68 is connected to a front end portion 24 of the attaching member 22, whereas the connecting member 30 is connected via an O-ring 26 to a rear end portion 25 of the attaching member 22. On the outer circumference of the rear end portion 25 and the connecting member 30, a thermistor (temperature sensor) 27 is provided to detect the temperature of the attaching member 22.

Figure 5A:
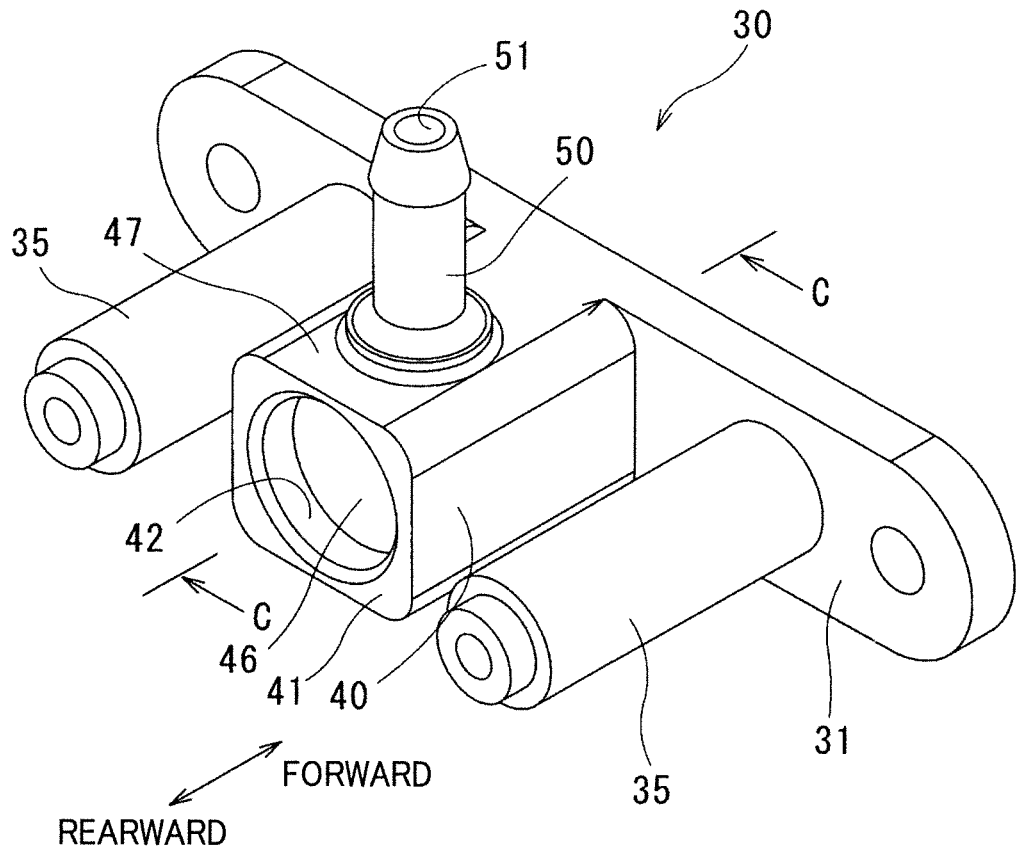
FIG. 5A is a perspective view of a connecting member viewed from behind.

As shown in FIG. 5A, the connecting member 30 is made of resin and includes a substrate 31, paired supporting legs 35, a sensor fixing portion 40, and an intermediate passage connecting portion 50.

Figure 5B:
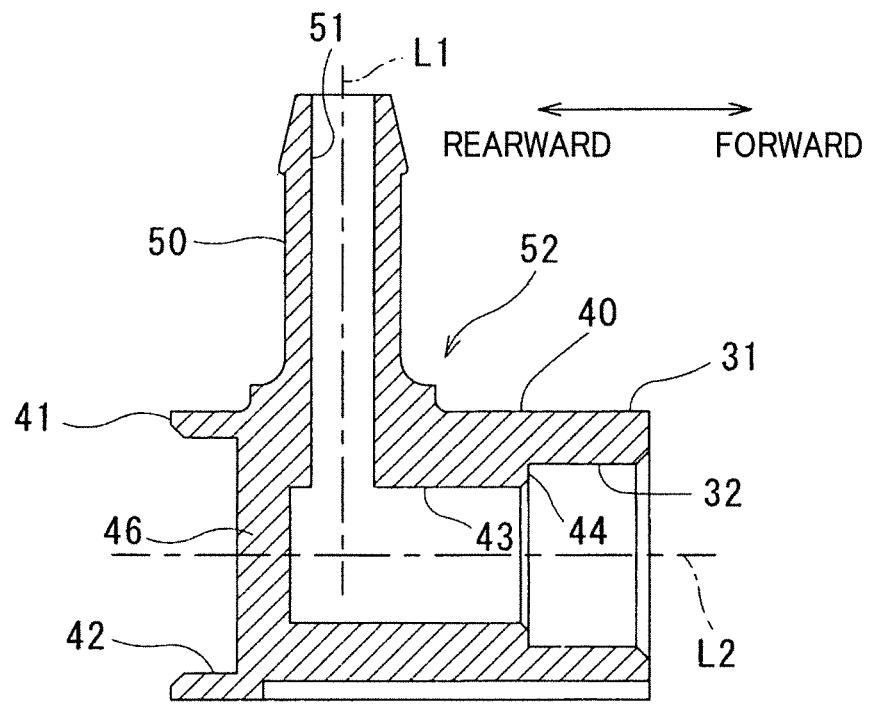
FIG. 5B is a cross section taken along a line C-C in FIG. 5A.

The substrate 31 is rectangular in shape as a whole, and each end thereof is semicircular in shape. At a central part in the longitudinal direction of the substrate 31, as shown in FIG. 5B, a through hole 32 which is circular in cross section is formed to penetrate the substrate 31 in the thickness direction. Each supporting leg 35 is column-shaped, is orthogonal to the substrate 31, and extends rearward from the substrate 31.

The sensor fixing portion 40 is provided between the paired supporting legs 35. The sensor fixing portion 40 is a substantially quadrangular prism in shape, is orthogonal to the substrate 31, and extends rearward from a central part in the longitudinal direction of the substrate 31 in the same manner as the supporting legs 35. In an end face 41 of the sensor fixing portion 40, a recess 42 which is circular in cross section is formed. In the sensor fixing portion 40, a second passage 43 which is circular in cross section is formed. The diameter of the second passage 43 is shorter than the diameter of the through hole 32, and the second passage 43 communicates with the through hole 32 via a stepped portion 44. An erected wall 46 between the recess 42 and the second passage 43 is a later-described opaque transmission window 46 (blocking visible light) of the optical sensor 61 provided in the recess 42.

The intermediate passage connecting portion 50 is a cylindrical nozzle orthogonally protruding from an outside wall 47 of the sensor fixing portion 40. The axial direction of the intermediate passage connecting portion 50 is orthogonal to the axial direction of the supporting leg 35 and the sensor fixing portion 40 and to the longitudinal direction of the substrate 31. A third passage 51 formed in the intermediate passage connecting portion 50 communicates with the second passage 43. Between the second passage 43 and the third passage 51 which are parts of the later-described oxygen supply passage 53, a bent portion 52 which is bent at right angle is formed. With this arrangement, the axis L1 of the third passage 51 is orthogonal to the axis L2 of the through hole 32 and the second passage 43. Furthermore, the recess 42 is formed at a location which is on an extension of the axis L2 of the through hole 32 and the second passage 43 and in the bent portion 52.

When the connecting member 30 is attached to the apparatus main body 11, as shown in FIG. 3, the rear end portion 25 of the attaching member 22 is inserted into the through hole 32. As a result, the first passage 23 communicates with the second passage 43. Furthermore, as the intermediate passage 15 is connected to the intermediate passage connecting portion 50, the third passage 51 communicates with the intermediate passage 15. The first passage 23, the second passage 43, and the third passage 51 constitute the oxygen supply passage 53. This oxygen supply passage 53 is bent at right angle on account of the bent portion 52 which is formed between the second passage 43 and the third passage 51.

The optical sensor 61 is provided between the recess 42 and the fixed plate 60. The optical sensor 61 is provided in the oxygen concentrating apparatus 10 and on an extension of the first passage 23 and the second passage 43. When the cannula 68 is on fire, the optical sensor 61 detects, through the transmission window 46, light propagated in the oxygen supply passage 53. The transmission window 46 is opaque but allows light to transmit therethrough, and is provided between the second passage 43 and the optical sensor 61.

Figure 6A:
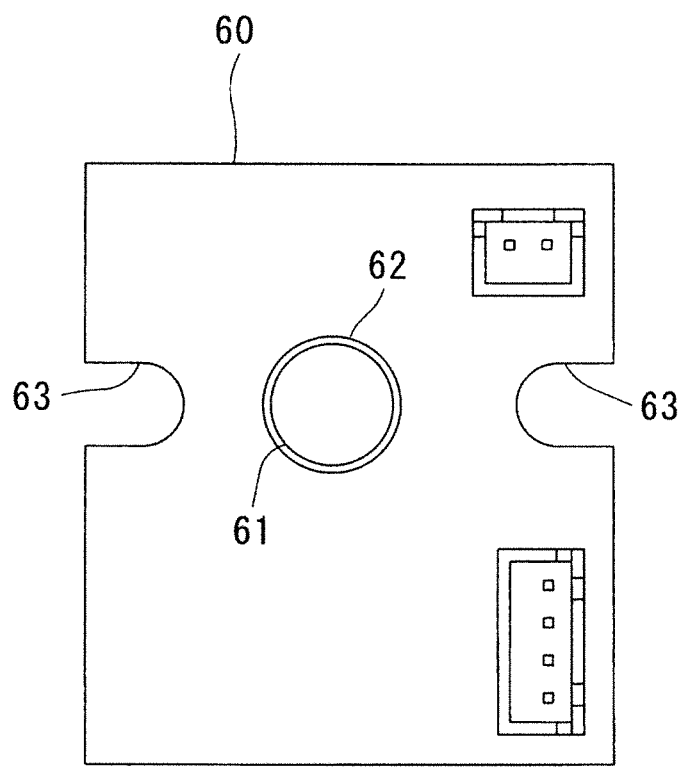
FIG. 6A shows a fixing plate viewed in front.
Figure 6B:
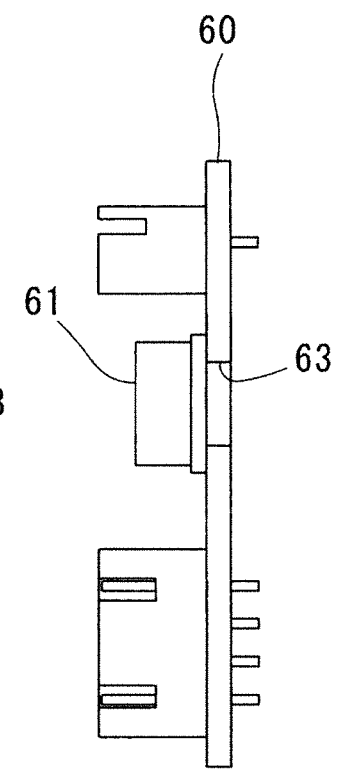
FIG. 6B is a side view of FIG. 6A.
Figure 7:
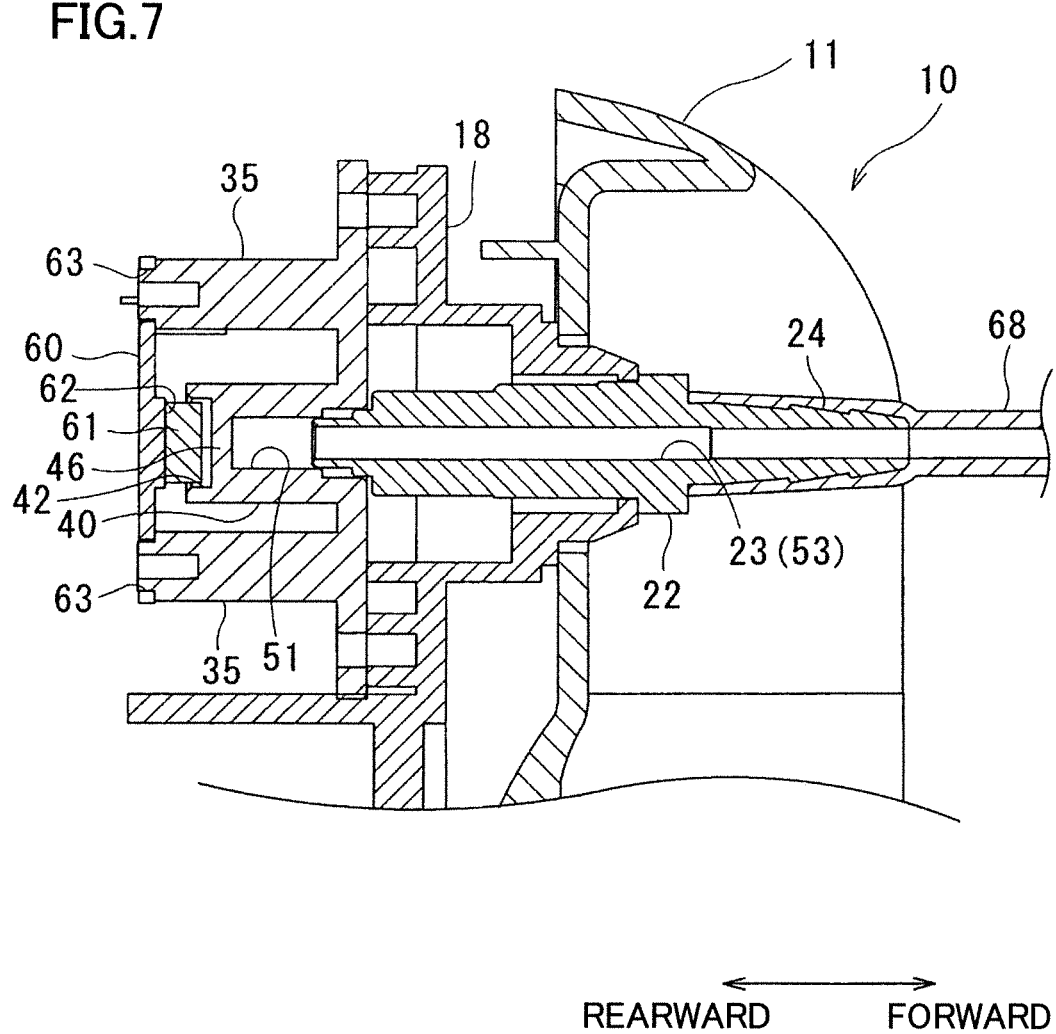
FIG. 7 is a cross section taken along a line B-B in FIG. 2.

As shown in FIG. 6A and FIG. 6B, the fixed plate 60 is rectangular in shape. A sensor arrangement portion 62 and cut parts 63 are formed in the fixed plate 60. The sensor arrangement portion 62 is provided at a central part of the fixed plate 60, and the optical sensor 61 is provided in this portion. The cut parts 63 are formed at side end faces of the fixing plate and each of which is curved toward the sensor arrangement portion 62. As shown in FIG. 7, when the fixed plate 60 is attached to the apparatus main body 11, the periphery of each cut part 63 is fixed to the leading end portion of the supporting leg 35 by a screw. With this arrangement, the optical sensor 61 can be provided between the sensor arrangement portion 62 and the recess 42 and fixed.

When the oxygen concentrating apparatus 10 is activated, oxygen generated by the oxygen generator 14 reaches the third passage 51 via the intermediate passage 15. The flow of the oxygen having reached the third passage 51 changes its direction at right angle at the bent portion 52, and the oxygen flows in the second passage 43 and the first passage 23 in order. The oxygen is then discharged from the apparatus main body 11 and is supplied to the patient via the cannula 68.

When the cannula 68 is on fire, the optical sensor detects, through the transmission window 46, light propagated in the oxygen supply passage 53.

Characteristics of Oxygen Concentrating Apparatus of Present Embodiment

The oxygen concentrating apparatus 10 of the present embodiment has the following characteristics.

In the oxygen concentrating apparatus 10 of the present embodiment, the optical sensor 61 is provided in the oxygen concentrating apparatus 10 and on an extension of the second passage 43 of the attaching member 22. In other words, the optical sensor 61 is upstream of the attaching member in the flow direction of the oxygen. Because smoke generated by the fire on the cannula 68 flows downstream in the flow direction of the oxygen, light is detectable, without being blocked by the smoke, by the optical sensor 61 which is provided upstream in the flow direction of the oxygen, with the result that the detection of the fire is ensured. Furthermore, because the optical sensor 61 is provided on the extension of the second passage 43 and hence light generated by fire is not blocked by the oxygen supply passage 53, the optical sensor 61 is able to reliably detect the fire.

In the oxygen concentrating apparatus 10 of the present embodiment, the transmission window 46 which is opaque and blocks visible light is provided, and the optical sensor 61 which is a photo diode or the like capable of detecting an infrared region is used as a photodetector. For this reason, influences of ambient light such as sunlight and illumination light are restrained and erroneous detection is prevented as compared to cases where a visible light sensor configured to receive only visible light is employed. Furthermore, because the transmission window 46 is provided between the second passage 43 and the optical sensor 61, adhesion of impurities such as dust to the optical sensor 61 is prevented.

In the oxygen concentrating apparatus 10 of the present embodiment, the attaching member 22 is made of metal with a high thermal conductivity, and the temperature sensor 27 is provided. It is therefore possible to detect fire by heat, in addition to the optical sensor 61.

In the oxygen concentrating apparatus 10 of the present embodiment, the oxygen supply passage 53 is bent at right angle and is therefore compactly disposed.

While the embodiment of the present invention has been described based on the figures, the scope of the invention is not limited to the above-described embodiment. The scope of the present invention is defined not by the above embodiment but by claims set forth below, and shall encompass the equivalents in the meaning of the claims and every modification within the scope of the claims.

While in the embodiment above the attaching member 22 is made of metal, this member may be made of another material such as resin.

The invention claimed is:

1. An oxygen concentrating apparatus comprising:
   an oxygen supply source;
   an attaching member, an oxygen discharger being attached to the attaching member while oxygen from the oxygen supply source is supplied to the oxygen discharger;
   an oxygen supply passage including at least a first passage formed in the attaching member; and
   a photodetector disposed in the oxygen concentrating apparatus and on a longitudinal axis of the first passage, the photodetector provided upstream along a flow direction of oxygen flowing in the first passage.

2. The oxygen concentrating apparatus according to claim 1, wherein,
   in response to the photodetector detecting fire on the oxygen discharger, supply of the oxygen is stopped.

3. The oxygen concentrating apparatus according to claim 1, wherein,
   an opaque transmission window is provided between the oxygen supply passage and the photodetector, the opaque transmission window allowing light to pass therethrough, and
   the photodetector includes an optical sensor detecting light through the transmission window, the optical sensor being capable of detecting an infrared region of light.

4. The oxygen concentrating apparatus according to claim 1, wherein,
   the attaching member is made of metal and includes a temperature sensor.

5. The oxygen concentrating apparatus according to claim 1, wherein,
   the oxygen supply passage includes a bent portion that is bent at a right angle, and
   an opaque transmission window is provided between the oxygen supply passage and the photodetector at the bent portion, the opaque transmission window allowing light to pass therethrough.

6. The oxygen concentrating apparatus according to claim 1, further comprising
   a connecting member connected to the attaching member,
   the oxygen supply passage including at least the first passage and a second passage, the second passage linearly communicating with the first passage and being formed in the connecting member, and
   the photodetector being provided upstream along the flow direction of oxygen flowing in the second passage and the first passage in order.

7. The oxygen concentrating apparatus according to claim 2, wherein,
   an opaque transmission window is provided between the oxygen supply passage and the photodetector, the opaque transmission window allowing light to pass therethrough, and
   the photodetector includes an optical sensor detecting light through the transmission window, the optical sensor being capable of detecting an infrared region of light.

8. The oxygen concentrating apparatus according to claim 2, wherein,
   the attaching member is made of metal and includes a temperature sensor.

9. The oxygen concentrating apparatus according to claim 2, wherein,
   the oxygen supply passage includes a bent portion that is bent at a right angle, and
   an opaque transmission window is provided between the oxygen supply passage and the photodetector at the bent portion, the opaque transmission window allowing light to pass therethrough.

10. The oxygen concentrating apparatus according to claim 3, wherein,
    the attaching member is made of metal and includes a temperature sensor.

11. The oxygen concentrating apparatus according to claim 3, wherein,
    the oxygen supply passage includes a bent portion that is bent at a right angle, and
    an opaque transmission window is provided between the oxygen supply passage and the photodetector at the bent portion, the opaque transmission window allowing light to pass therethrough.

12. The oxygen concentrating apparatus according to claim 4, wherein,
    the oxygen supply passage includes a bent portion that is bent at a right angle, and
    an opaque transmission window is provided between the oxygen supply passage and the photodetector at the bent portion, the opaque transmission window allowing light to pass therethrough.

* * * * *